United States Patent [19]

VandenBerg

[11] Patent Number: Plant 6,904

[45] Date of Patent: Jul. 4, 1989

[54] CHRYSANTHEMUM PLANT NAMED NACIDO

[75] Inventor: Cornelis P. VandenBerg, Salinas, Calif.

[73] Assignee: Yoder Brothers, Inc., Ashtabula, Ohio

[21] Appl. No.: 187,579

[22] Filed: Apr. 28, 1988

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Nacido particularly characterized by its flat capitulum form; decorative capitulum type; yellow ray floret color; diameter across face of capitulum of up to 5 cm at maturity; uniform eight week photoperiodic flowering response to short days; peduncle length ranging from 8 to 15 cm on open, terminal sprays; medium plant height when grown as a single stem spray cut mum; and good tolerance to high temperatures for bud initiation and flower development.

3 Drawing Sheets

The present invention comprises a new and distinct cultivar of Chrysanthemum, botanically known as *Dendranthema grandiflora,* and referred to by the cultivar name Nacido.

Nacido, identified as 85877006, was originated from a cross made by Cornelis P. VandenBerg in a controlled breeding program in Salinas, Calif. in 1984.

The female parent and the male parent of Nacido were both unnamed seedlings, identified respectively as 75222009 and 79C08001.

Nacido was discovered and selected as one flowering plant within the progeny of the stated cross by Cornelis P. VandenBerg in September 1985 in a controlled environment in Salinas, Calif.

The first act of asexual reproduction of Nacido was accomplished when vegetative cuttings were taken from the initial selection in November 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Nacido are firmly fixed and are retained through successive generations of asexual reproduction.

Nacido has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The high temperature tolerance was determined in flowerings in Louisville, Ky., and in a simulated high temperature environment in Salinas, Calif.

The following traits have been repeatedly observed and are determined to be basic characteristics of Nacido, which, in combination, distinguish this Chrysanthemum as a new and distinct cultivar:

1. Flat capitulum form.
2. Decorative capitulum type.
3. Yellow ray floret color.

4. Diameter across face of capitulum up to 5 cm at maturity.
5. Uniform eight week photoperiodic flowering response to short days.
6. Peduncle length ranging from 8 to 15 cm on open terminal sprays.
7. Medium plant height, requiring 1 to 2 long day weeks prior to short days to attain a flowered plant height of 90 to 100 cm for year-round flowerings.
8. Good tolerance to high temperatures for bud initiation and flower development.

The accompanying photographic drawings show typical inflorescence and leaf characteristics of Nacido, with the colors being as nearly true as possible with illustrations of this type.

Sheet 1 is a color photograph of Nacido grown as a single stem cut spray mum.

Sheet 2 is a black and white photograph of three views of the inflorescence of Nacido.

Sheet 3 is a black and white photograph showing the upper and under sides of the leaves of Nacido at three stages of development (mature, intermediate and immature).

Of the commercial cultivars known to the inventor, the most similar in comparison to Nacido is Gleam, disclosed in U.S. Plant Pat. No. 5,713. Reference is made to Chart A, which compares certain characteristics of Nacido to the same characteristics of Gleam. Similar traits are ray floret color, capitulum form and type, and spray formation, with Nacido having shorter peduncles. The diameter of capitulum of Nacido is smaller, flowering response is faster and high temperature tolerance is better than Gleam. Nacido requires more long days than Gleam to attain a plant height of 90 to 100 cm.

In the following description, color references are made to The Royal Horticultural Society Colour Chart. The color values were determined on plant material grown in Salinas, Calif. on Oct. 12, 1987.

Classification:

*Botanical.*—*Dendranthema grandiflora,* cv. Nacido.

*Commercial.*—Decorative cut spray mum.

INFLORESCENCE

A. Capitulum:

*Form.*—Flat.

*Type.*—Decorative.

*Diameter across face.*—Up to 5 cm at maturity.

B. Corolla of ray florets:

*Color (general tonality from a distance of three meters).*—Yellow.

*Color (upper surface).*—12A.

*Color (under surface).*—9A.

*Shape.*—Cross section of ray, concave. Longitudinal axis, straight. Tip of ray, oblong, slightly indented.

C. Corolla of disc florets:

*Color (mature).*—Closest to 5A.

*Color (immature).*—Closest to 151B. Very few disc florets, not visible in mature flower.

D. Reproductive organs:

*Androecium.*—Present on disc florets only; no pollen.

*Gynoecium.*—Present on both ray and disc florets.

PLANT

A. General appearance:

*Height.*—Medium; 90 to 100 cm as a single stem cut mum with 1 to 2 long day weeks prior to short days.

B. Foliage:

*Color (upper surface).*—147A.

*Color (under surface).*—147B.

*Shape.*—Deeply lobed and serrated.

CHART A4

COMPARISON OF NACIDO AND GLEAM

| | Nacido | Gleam |
|---|---|---|
| Ray floret color | Yellow | Yellow |
| Capitulum form and type | Flat Decorative | Flat Decorative |
| Spray formation | Terminal 8 to 15 cm peduncles | Terminal 20 to 35 cm peduncles |
| Diameter across face of capitulum | Up to 5 cm | 5 to 7 cm |
| Plant height | Medium | Tall |
| Flowering response period | 8 weeks | 9 weeks |
| High temperature tolerance | Good | Marginal to poor |

COMPARISONS MADE OF PLANTS GROWN AS SINGLE STEM SPRAY CUT MUMS IN SALINAS, CALIFORNIA

I claim:

1. A new and distinct Chrysanthemum plant named Nacido, as described and illustrated, and parts thereof.

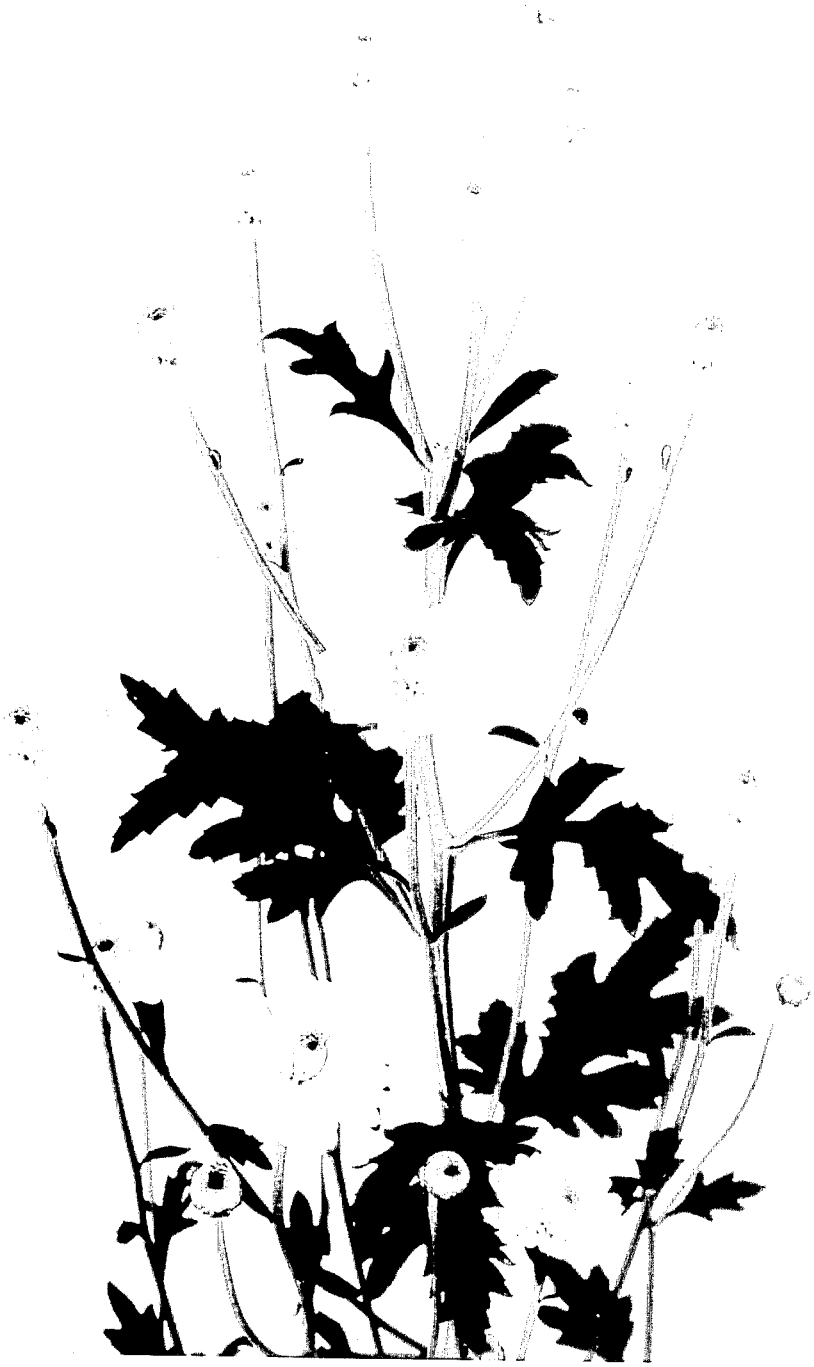

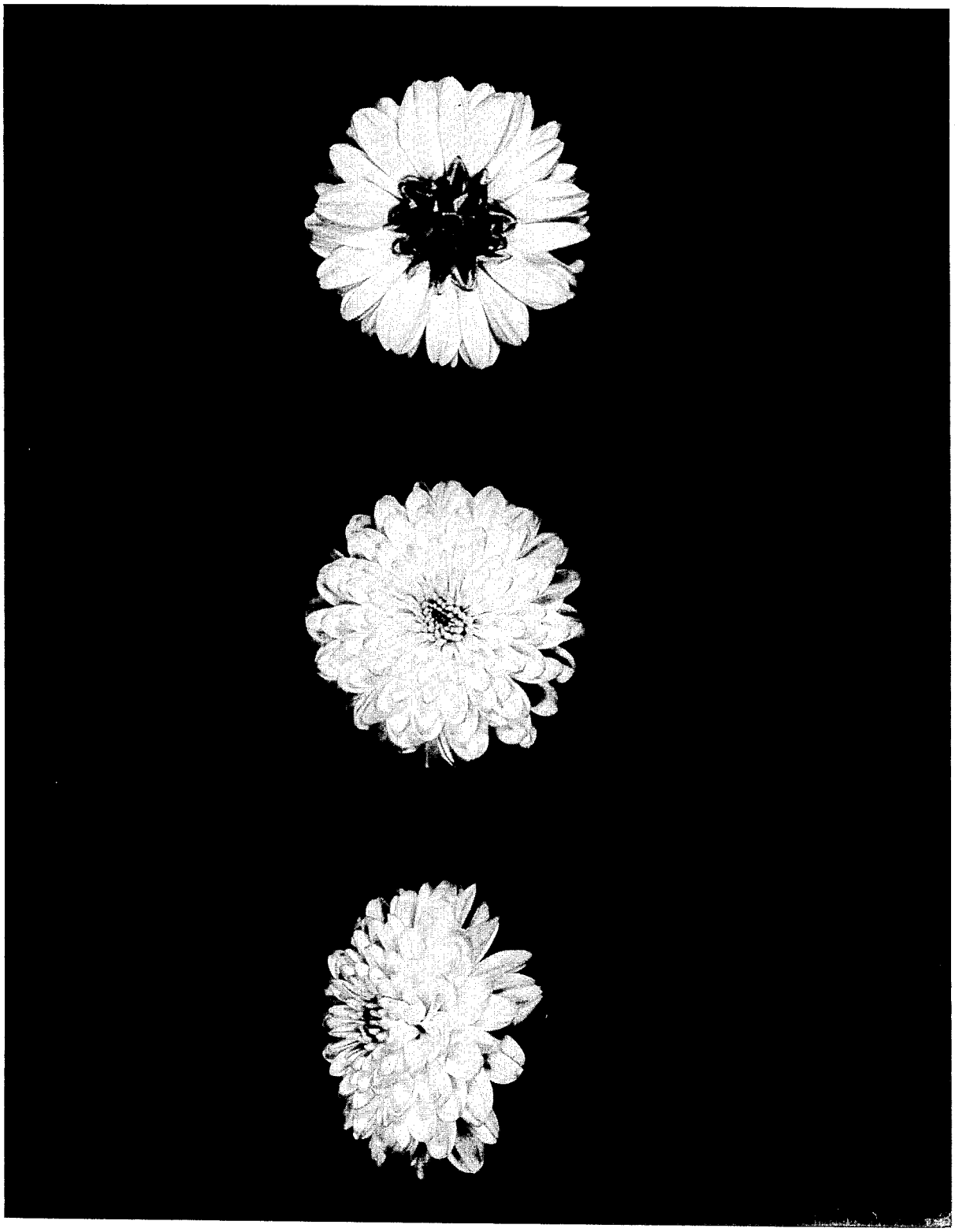

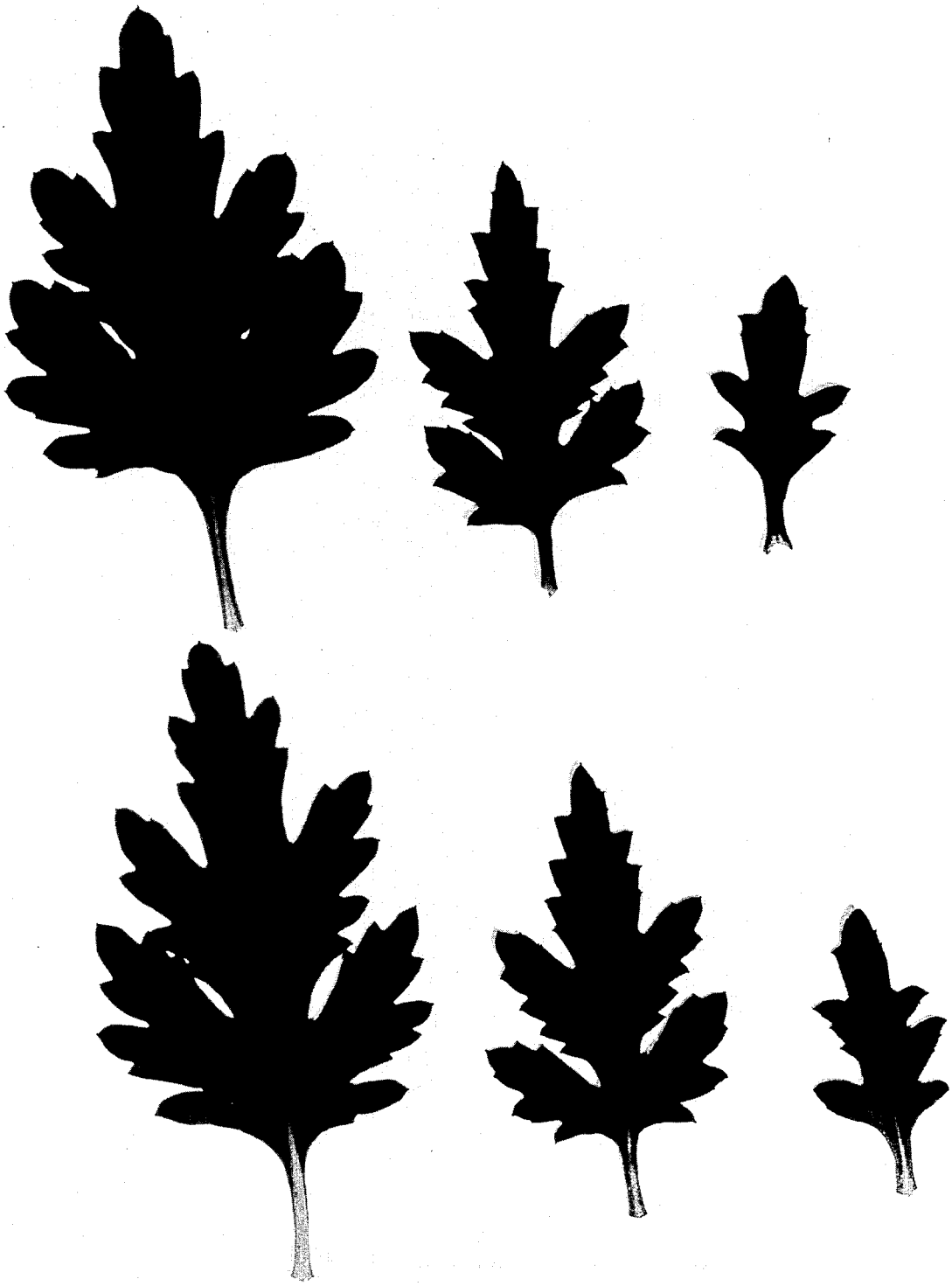

* * * * *